United States Patent [19]

Beebe et al.

[11] Patent Number: 4,611,643
[45] Date of Patent: Sep. 16, 1986

[54] INTERLOCKING FLUID TRANSFER DEVICE AND RESULTING ASSEMBLY

[75] Inventors: Susan M. Beebe, Glencoe; T. Michael Dennehey; Robert J. Kruger, both of Arlington Heights; Brian D. Zdeb, Round Lake Park, all of Ill.

[73] Assignee: Baxter Travenol Laboratories, Inc., Deerfield, Ill.

[21] Appl. No.: 553,737

[22] Filed: Nov. 21, 1983

[51] Int. Cl.$^4$ .............................................. B65B 3/04
[52] U.S. Cl. ................................. 141/311 R; 285/41; 604/905
[58] Field of Search .................... 137/798; 141/1, 11, 141/82, 85, 311 R, 382; 251/142; 285/41; 604/905

[56] References Cited

U.S. PATENT DOCUMENTS

| | | | |
|---|---|---|---|
| 1,921,809 | 8/1933 | Crain | 138/89 |
| 2,782,496 | 2/1957 | Augustauskas | 29/469 |
| 2,903,004 | 9/1959 | Gerteis | 137/74 |
| 2,910,083 | 10/1959 | Cook | 137/74 |
| 3,493,002 | 2/1970 | Brugler et al. | 137/74 |
| 3,913,348 | 10/1975 | Magester | 62/298 |
| 3,968,195 | 7/1976 | Bishop | 264/154 |
| 3,986,508 | 10/1976 | Barrington | 604/411 |
| 4,004,586 | 1/1977 | Christensen et al. | 604/413 |
| 4,019,512 | 4/1977 | Tenczar | 604/411 |
| 4,022,205 | 5/1977 | Tenczar | 604/411 |
| 4,022,256 | 5/1977 | Berkman et al. | 141/1 |
| 4,030,494 | 6/1977 | Tenczar | 604/411 |
| 4,149,534 | 4/1979 | Tenczar | 604/403 |
| 4,157,723 | 6/1979 | Granzow et al. | 141/1 |
| 4,265,280 | 5/1981 | Ammann et al. | 141/98 |
| 4,298,001 | 11/1981 | Hargest et al. | 604/49 |
| 4,325,417 | 4/1982 | Boggs et al. | 141/98 |
| 4,334,551 | 6/1982 | Pfister | 134/614.03 |
| 4,340,097 | 7/1982 | Ammann et al. | 148/98 |

FOREIGN PATENT DOCUMENTS

WO82/02528  8/1982  PCT Int'l Appl. .
1428391  6/1972  United Kingdom .

Primary Examiner—Stephen Marcus
Assistant Examiner—Mark Thronson
Attorney, Agent, or Firm—Bradford R. L. Price; Daniel D. Ryan; Paul C. Flattery

[57] ABSTRACT

A tubular fluid transfer device is operative by itself to seal the end of a conduit. By coupling two of the devices together, a fluid path can be selectively established between two conduits by applying heat energy. The device includes a generally planar surface having a meltable region. The generally planar surface of one device is slidable against the generally planar surface of another one of the devices to bring the meltable regions into registration. The device includes a coupling mechanism which guides the meltable regions into the desired alignment as registration occurs. Furthermore, as the meltable regions register, the coupling mechanism generates forces which bias the meltable regions into intimate contact. The coupling mechanism thereafter releasably retains the devices in this snug interlocked relationship, so that the energy can be applied to jointly heat the meltable regions and melt open a fluid path between the two devices.

5 Claims, 12 Drawing Figures

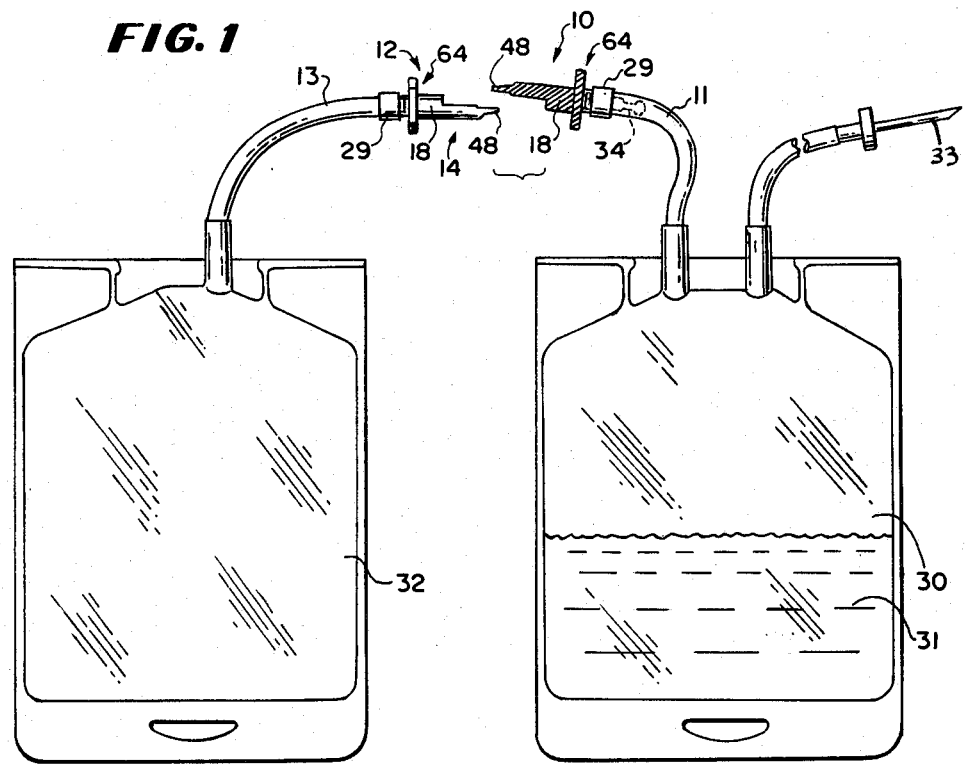
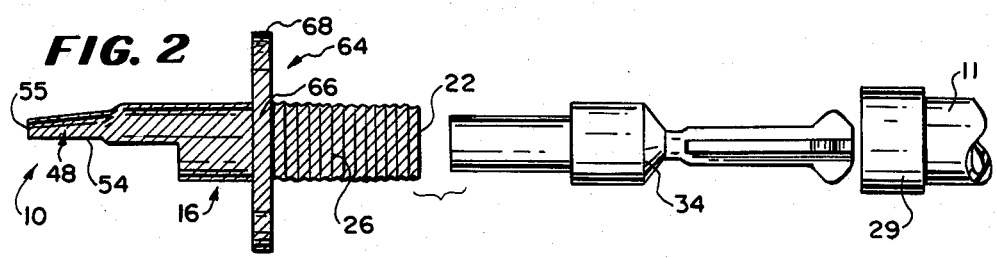
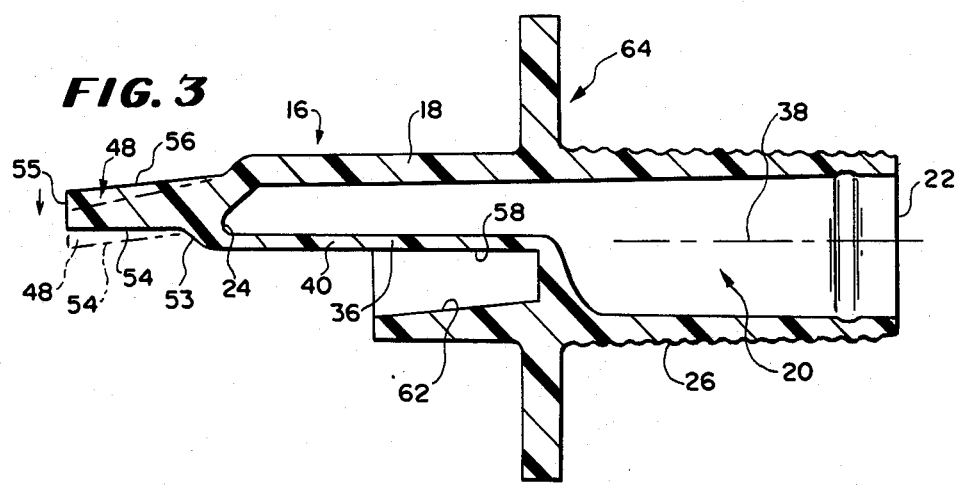

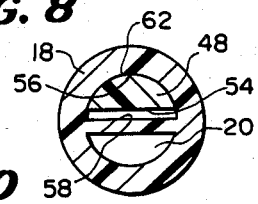
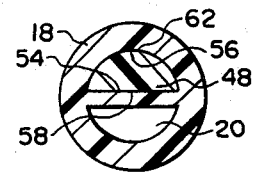
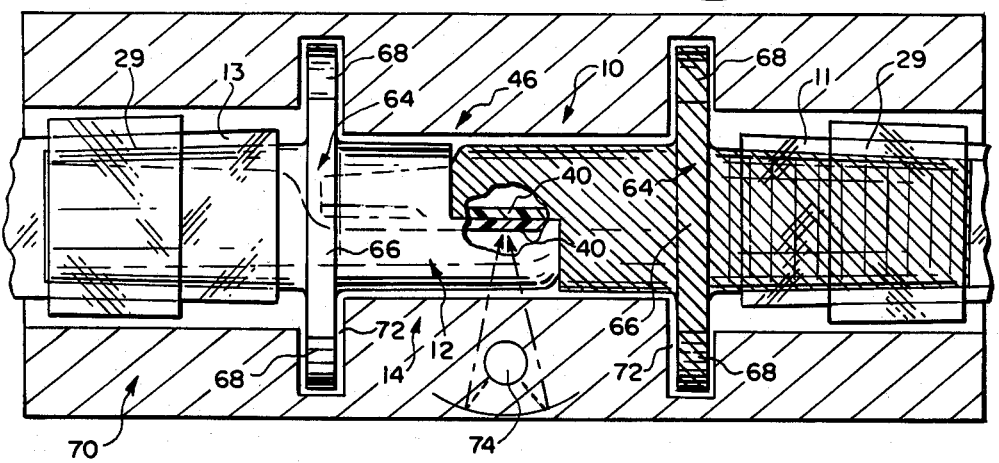
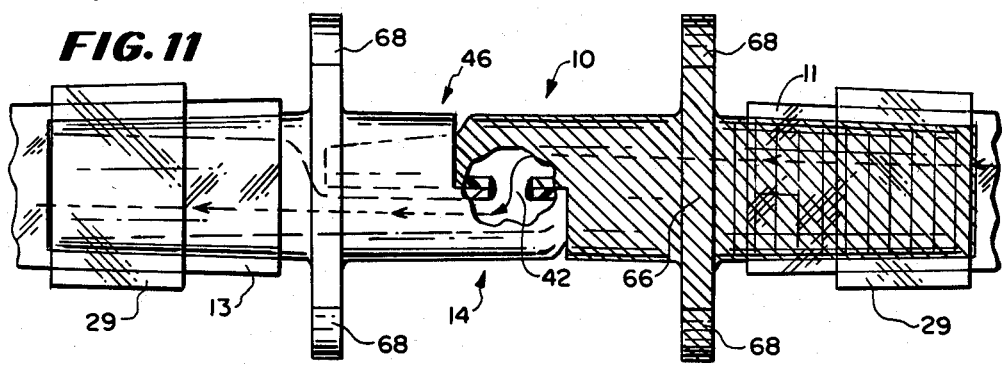
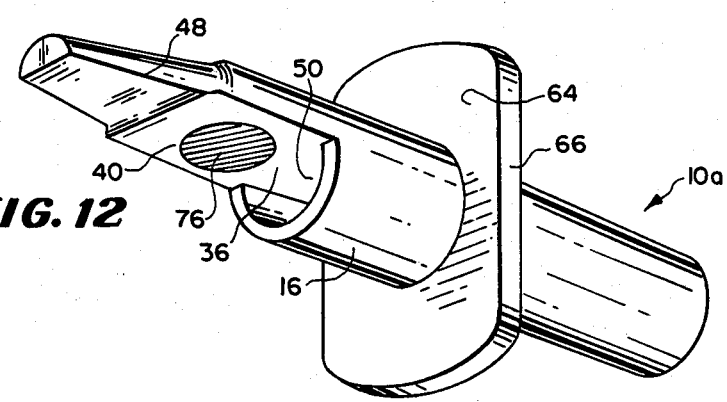

INTERLOCKING FLUID TRANSFER DEVICE AND RESULTING ASSEMBLY

FIELD OF THE INVENTION

This invention generally relates to fluid transfer devices. In particular, this invention relates to fluid transfer devices which include meltable portions.

BACKGROUND OF THE INVENTION

Gerteis U.S. Pat. No. 2,903,004 and Berkman et al U.S. Pat. No. 4,022,256 both concern fluid transfer devices which use a meltable wall to normally seal a conduit from communication with the atmosphere. By coupling two such devices together, heat can be transferred by conduction from an external source to melt both walls and open a fluid path between the assembled devices.

Granzow et al U.S. Pat. No. 4,157,723 concerns a fluid transfer device which uses a meltable, radiant energy absorbing wall to normally seal a conduit. By coupling two of these devices together and applying thermal radiation, the walls can be melted to form a fluid path between the assembled devices.

Other fluid transfer devices and assemblies which use meltable radiant energy absorbing walls are disclosed in the following U.S. patents:
  Ammann et al—U.S. Pat. No. 4,265,280
  Boggs et al—U.S. Pat. No. 4,325,417
  Ammann et al—U.S. Pat. No. 4,340,097

Fluid transfer devices which include meltable portions lend themselves to use in systems in which fluids are to be transferred in an aseptic or sterile manner; for example, in blood component collection and processing systems; in chemical compounding in parenteral solution formations systems; and in fluid systems associated with peritoneal dialysis.

Because these systems can involve the transfer of human blood and sterile parenteral solutions, it is desirable that the performance characteristics of the transfer devices and assemblies be optimized to the greatest extent possible.

SUMMARY OF THE INVENTION

A fluid transfer device is provided which is operative by itself to seal the end of a conduit. By coupling two of the devices together, a fluid path can be selectively established between two conduits.

The device which embodies the features of the invention includes a generally tubular body having a sidewall which peripherally encloses a bore. The bore has an open end and an oppositely spaced closed end. The open end is attachable to the end of a fluid conduit. The oppositely spaced closed end seals the attached conduit.

In accordance with one aspect of the invention, the sidewall includes a generally planar surface portion which has a centerline extending axially of the bore. The generally planar surface portion includes a region which, when heated, is meltable to form an opening communicating with the bore. The planar surface portion of one of the devices can be slid against the planar surface portion of a second one of the devices to bring two meltable regions into registration. By applying energy sufficient to heat and melt the overlying regions, a fluid path can be established between the two coupled devices.

In accordance with another aspect of the invention, the device includes coupling means which guides the meltable regions into the desired alignment as registration occurs. Furthermore, as the meltable regions register, the coupling means is operative for biasing the regions into intimate contact. The coupling means releasably retains this snug relationship between the devices until energy can be applied to open the fluid path between the devices.

In a preferred embodiment, the energy applied to heat the meltable regions is radiant energy.

Other features and advantages of the invention will be pointed out in, or will be apparent from, the specification and claims, as will obvious modification of the embodiments shown in the drawings.

DESCRIPTION OF THE DRAWINGS

FIG. 1 is a blood collection assembly of two bags, each of which includes the tubular fluid transfer device which embodies the features of the invention;

FIG. 2 is an enlarged and exploded view of one of the fluid transfer devices shown in FIG. 1;

FIG. 3 is a side section view of the fluid transfer device shown in FIG. 2;

FIG. 8 is a transverse section view taken generally along line 8—8 in FIG. 6;

FIG. 9 is a transverse section view taken generally along line 9—9 in FIG. 7;

FIG. 10 is a view, with portions broken away and in section, of the two coupled fluid transfer devices positioned in a device which applies energy sufficient to heat the meltable regions and form a fluid path between the devices;

FIG. 11 is a view of the two coupled devices, with a portion broken away and in section, after the fluid path has been established between them; and FIG. 12 is a perspective view of an alternate embodiment of the device which embodies the features of the invention.

Figure 4:
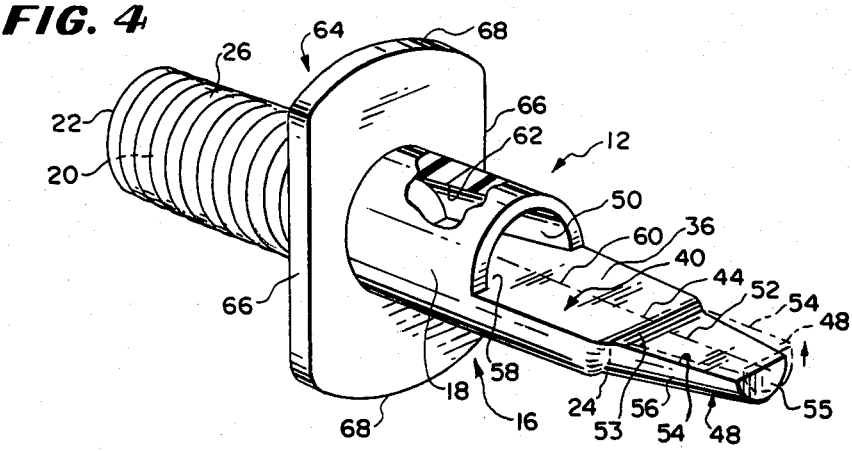
FIG. 4 is a perspective view, with a portion broken away and in section, of the other fluid transfer device shown in FIG. 1.

Before explaining the embodiments of the invention in detail, it is to be understood that the invention is not limited in its application to the details of construction and the arrangement of components set forth in the following description or illustrated in the accompanying drawings. The invention is capable of other embodiments and of being practiced or carried out in various ways. Furthermore, it is to be understood that the phraseology and terminology employed is for the purpose of description and should not be regarded as limiting.

DESCRIPTION OF THE PREFERRED EMBODIMENTS

A fluid transfer device 10 which embodies the features of the invention is shown in FIGS. 2 and 3. The device 10 is attachable to a conduit 11 to normally seal the conduit 11 from communication with the atmosphere.

As shown in FIGS. 1 and 5 through 7, two of the devices 10 and 12, each identical in configuration and each attached to a conduit 11 and 13, can be connected together to form a fluid transfer assembly 14.

As will be described in greater detail later, and as shown in FIGS. 10 and 11, a fluid path can be selectively opened between the two attached devices 10 and 12, and thus between the associated conduits 11 and 13.

Each of the devices 10 and 12 thus has utility by itself, as a means for sealing the end of a conduit 11 and 13. The assembly 14 of the devices 10 and 12 also has utility, as a means for coupling and for transferring fluid between a pair of previously unconnected conduits.

Both devices 10 and 12 shown in FIG. 1 are identical in overall configuration. The configuration of the device 10 is shown in greater detail in FIGS. 2 and 3. The matching configuration of the device 12 is shown in greater detail in FIG. 4. The same reference numerals are used to identify common elements.

Each device 10 and 12 includes a generally tubular body 16 which includes a sidewall 18 peripherally enclosing a bore 20. One end 22 of the bore 20 is opened, and the body 16 is attachable at this bore end 22 to the associated fluid conduit 11 and 13. Fluid communication between the associated conduit 11 and 13 and the bore 20 is thus established.

The oppositely axially spaced end 24 of the bore 20 is closed. By attaching the device 10 and 12 to the associated conduit 11 and 13, then, the conduit 11 and 13 is itself sealed.

Each device 10 and 12 may be variously attached to the end of the conduit 11 and 13. In the illustrated embodiment, a hermetic, friction-fit between the conduit 11 and 13 and the opened bore end 22 is envisioned. For this purpose, the body 16 surrounding the open bore end 22 includes ridges 26, or is otherwise suitably roughened, to frictionally grip the conduit 11 and 13. An elastic band 29 (see FIG. 2) made, for example, from a latex material, preferably encircles the outer periphery of the junction between the body 16 and the conduit 11 and 13 to assure a fluid-tight hermetic fit.

Alternately, if the material of the conduit 11 and 13 and the material from which the device 10 and 12 is fabricated are compatible, a solvent bond can be used to attach the device 10 and 12 to the conduit 11 and 13. Still alternately, a heat seal or an adhesive bond can be used for the same purpose.

As shown in FIG. 1, the conduit 11 and 13 to which the device 10 and 12 is attached can itself be integrally connected with a container 30 and 32. The one container 30 can contain a fluid 31. The other container 32 can be empty and be used to receive the fluid from the container 30 via the assembly 14.

In the specific embodiment shown in FIG. 1, the container 30 is pictured as a plastic bag for collecting whole blood. The bag 30 includes an integrally attached phlebotomy needle 33 which introduces whole blood from a donor into the bag 30. In this context, the fluid 31 is an anticoagulant for the whole blood introduced into the bag 30. The container 32 is pictured as a plastic bag into which components of whole blood centrifugally separated in the container 30 can be transferred for storage.

As shown in FIGS. 1 and 2, a manually operated inline valve member 34 is preferably provided to normally prevent fluid from entering the bore 20 of the device 10 until transfer is desired. While the valve member 34 may be variously constructed, in the illustrated embodiment, it takes the form of a manually frangible valve member, such as disclosed in Munsch U.S. Pat. No. 4,340,049.

Figure 5:
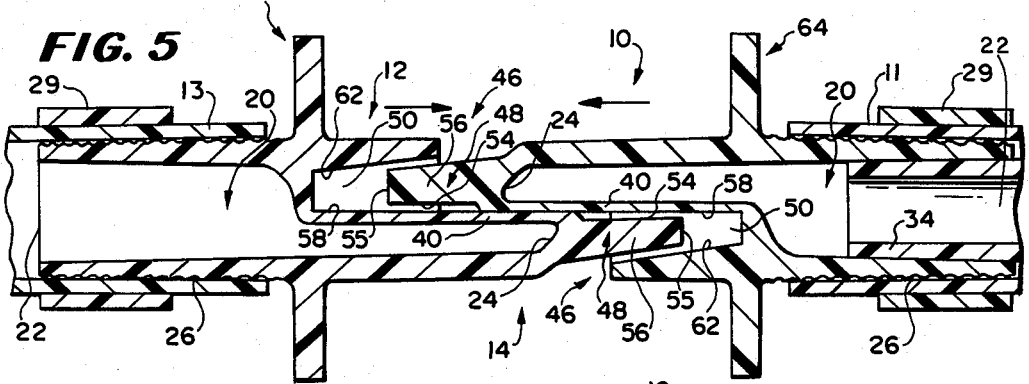
FIGS. 5, 6, and 7 are a sequence of sectional side views showing the two fluid transfer devices shown in FIG. 1 being coupled together.
Figure 6:
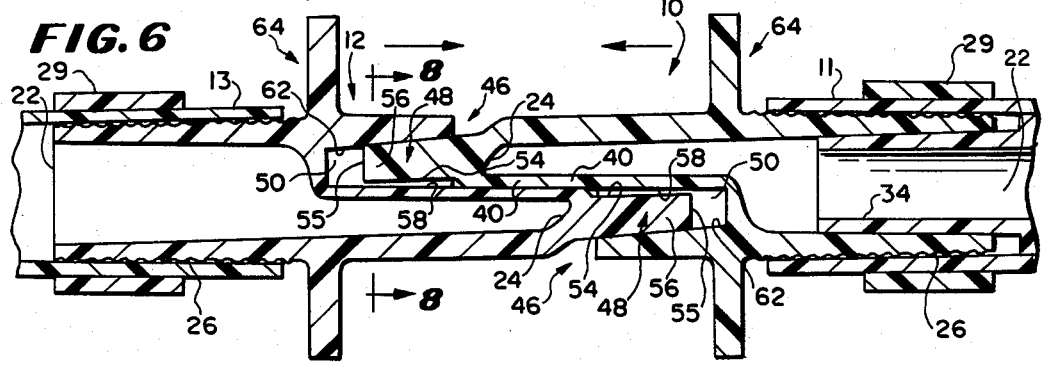
Figure 7:
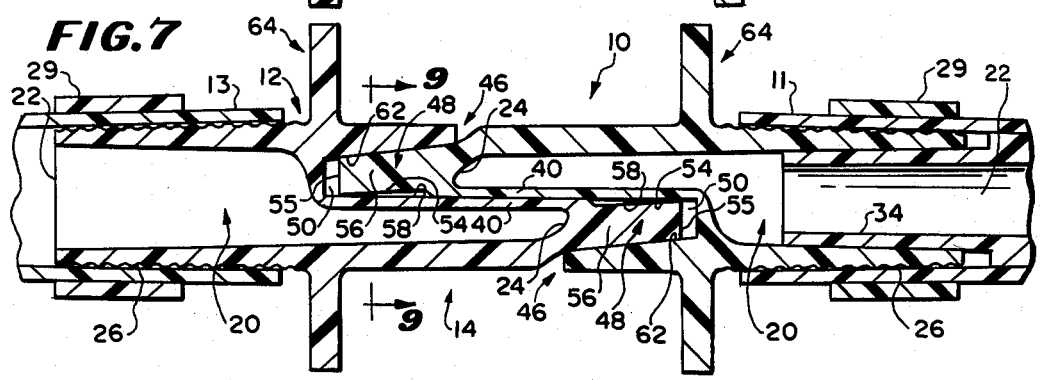

The valve member 34 may be frictionally fitted to the body 16 of the device 10, as shown in FIGS. 5 through 7. It may also be attached by means of a solvent or adhesive bond, by heat sealing, or by one piece molding.

In accordance with one aspect of the invention, as best shown in FIGS. 3 and 4, the sidewall 18 of the tubular body 16 of each device 10 and 12 includes a generally planar surface portion 36. The surface portion 36 extends rearwardly from the closed end 24 of the bore 20 in a plane which is generally parallel to the axis 38 of the bore 20 (see FIG. 3).

While various configurations can be used, due to the particular position of the planar surface portion 36 in the illustrated embodiment, the internal dimension of the bore 20 adjacent to its closed end 24 is about one-half the internal dimension of the bore 20 adjacent its open end 22.

The planar surface portion 36 includes a region 40 which, when heated, is meltable to form an opening communicating with the bore 20. Fluid can be conducted through this formed opening. The meltable region 40 is generally centered along the centerline 44 of the planar surface portion 36 (see FIG. 4). The meltable region 40 is also preferably positioned in close proximity to the closed end 24 of the bore 20 to minimize the size of the area between the formed opening and the closed bore end 24, in which fluid can become entrapped.

The region 40 preferably melts only at temperatures which result in the destruction of bacterial contaminants, i.e., over 200° C. In this preferred arrangement, the region 40 can be opened only in connection with an active sterilization step which serves to sterilize the regions adjacent to the fluid path as the fluid path is formed.

When the assembly 14 is formed (see FIG. 10), the meltable regions 40 of the two devices 10 and 12 are, by virtue of the features of the invention, aligned and placed in intimate facing contact. When jointly heated, both of the regions 40 melt, fusing the two devices 10 and 12 together. A fluid path 42 (see FIG. 11) is also opened between the two devices 10 and 12, and thus between the attached conduits 11 and 13.

More particularly, as shown in FIGS. 5 through 7, the assembly 14 is formed by sliding the planar surface portion 36 of one device 10 against the planar surface portion 36 of the other device 12, until the two meltable regions 40 come into registration.

In accordance with the invention, each device 10 and 12 includes coupling means 46 for establishing and thereafter maintaining proper alignment between the two planar surface portions 40 until registration occurs. At the same time, the coupling means 48 is operative for assuring that the desired degree of contact between the overlying regions 40 occurs. The coupling means 48 is also operative for releasably interlocking the regions 40 in this snug contiguous condition.

The energy applied to heat the regions 40 will thus be distributed uniformly upon and between the regions 40. Consistently uniform melting patterns will thus occur in the regions 40.

While the coupling means 46 may vary, in the illustrated and preferred embodiment (see, in particular, FIGS. 3 and 4), the coupling means 46 includes a tab 48 and a matching slot 50. The tab 48 extends axially beyond the closed end 24 of each device 10 and 12. The slot 50 arcuately spans a section of the planar surface portion 36 of each device 10 and 12.

As can be seen in FIGS. 5 through 7, as the planar surface portion 36 portion of the one device 10 is slid against the planar surface 36 of the second device 12, the tab 48 of the one device 10 telescopically mates with the slot 50 of the second device 12, and vice versa.

In accordance with the invention, however, the tab 48 and the slot 50 mate only when the centerlines 44 of the two planar surfaces 36 are in alignment. When the centerlines 44 are not in alignment, the slot 50 and tab 48 interfere, preventing the two planar surfaces 36 from being slid against each other. It is thus not possible to bring the meltable regions 40 into registration until the centerlines 44 do align.

Furthermore, also in accordance with the invention, as each tab progressively enters the slot 50, bringing the meltable regions 40 successively closer into registration, a force is developed which biases the meltable regions 40 into intimate contact. Still further, as the meltable regions 40 are biased into intimate contact, the tab 48 and slot 50 frictionally interlock. Subsequent lateral, transverse, or rotational movements of the interlocked devices 10 and 12 are resisted.

The particular mating configurations of the tab 48 and slot 50 can vary. However, in the illustrated and preferred embodiment (see, in particular, FIG. 4), the tab 48 takes the shape of a truncated cone having an axis 52 which is centered with respect to the centerline 44 of the planar surface portion 36. The truncation of the conical shape of the tab 48 occurs both along its axis 52 in a plane generally perpendicular to its base 53, thereby forming a planar surface 54, as well as transversely of its axis 52 in a plane generally parallel its base 53, thereby forming a planar end surface 55. Another way of describing the tab 48 is as a frustum which has been split in half along the longitudinal axis 52, i.e., along the planar surface 54.

In addition to the planar surfaces 54 and 55, due to its truncated conical shape, the tab 48 includes an arcuate surface 56 which extends radially outwardly from the axis 52. The arcuate surface 56 tapers toward the axis 52 in a direction away from the closed end 24 of the bore 20.

As best shown in FIG. 3, while the planar tab surface 54 is generally parallel to the planar body surface portion 36, the two surfaces 54 and 36 are themselves not coplanar. Instead, the planar tab surface 54 is offset in the direction of the bore 20 away from the planar body surface portion 36.

As shown by arrows and in phantom lines in FIGS. 3 and 4, the tab 48 of each device 10 and 12 is resiliently deformable relative to the body 16 out of its normal position in response to external force in a direction transverse of the axis 52.

The interior configuration of the slot 50, like the exterior configuration of the tab 48, constitutes a cone which has been truncated in two planes. The slot 50 thus includes a generally planar surface 58, the axis 60 of which is centered along the centerline 44 of the planar surface 36 (see FIG. 4), as well as an arcuate surface 62, which extends radially outwardly from the axis 60 and which tapers toward the axis 60 in a direction toward the open end 22 of the bore 22. The slope and taper of the arcuated slot surface 62 correspond with the slope and taper of the arcuate tab surface 56.

The tab 48 of the device 10 will thus uniquely mate with the slot 50 of the device 12, and vice versa, but only when the centerlines 52 and 60 of the tab 48 and slot 50, and thus the centerline 44 of the planar surfaces 36 themselves, are aligned. When the centerlines 44 do not align, the tab 48 and slot 50 do not mate. Instead, the planar end surface 55 of the tab 58 abuts against the entrance of the slot 50.

However, once telescopically mated, the tab 48 and slot 50 cooperate (see FIGS. 8 and 9) to retain the centerlines 44 in the proper aligned relationship. Any movement of the devices 10 and 12 either transversely of the aligned centerlines 44 or perpendicularly of the aligned centerlines 44 is resisted. Proper alignment between the centerlines 44 of the devices 10 and 12 is thus assured as the meltable regions 40 are moved toward registration. In this respect, the coupling means 48 can be considered to be "self-aligning."

In addition, as shown in FIGS. 6 and 8, as the tab 48 moves progressively into the slot 50, the arcuate surface 56 of the tab 48 progressively presses against the sloped arcuate surface 62 of the slot 50. This is because, as heretofore described, the planar tab surface 54 is purposely offset from planar body surface portion 36. As the tab 48 is moved ever deeper into the slot 50, the area of pressing contact increases. Because, as also heretofore described, the tab 48 is resiliently deformable, as the pressing contact increases, the arcuate slot surface 62 progressively deflects the deformable tab 48 toward the facing planar surface 58 (see FIGS. 7 and 9). This camming action between the tab 48 and the slot 50 occurs simultaneously at each end of the assembly 14.

As a result, a force is applied upon the tab 48 of each device 10 and 12. The applied forces mutually interact to bias the meltable regions 40 toward snug, intimate contact as registration occurs.

To further promote the desired degree of intimate contact between the meltable regions 40, the meltable region 40 of either one or both devices 10 and 12 can be outwardly bowed or otherwise elevated slightly along its centerline 44 by not more than about 0.01 inch, and preferably by about 0.002 to 0.003 inch. This slightly outwardly bowed, or convex configuration can be confined only to the meltable region 40, or it can extend uniformly along the centerline 40 of the surface portion 36. In either case, the use herein of the term "generally planar" to describe the surface portion 36 is intended to encompass this alternate, slightly convex configuration of the meltable region 40.

As the above-described camming action between the tab 48 and the slot 50 continues, an interference fit progressively develops along the interface between the arcuate tab portion 56 and the arcuate slot surface 62. The interference fit frictionally interlocks the two devices 10 and 12 together as intimate contact occurs.

The devices 10 and 12 thus become releasably interlocked both along and transversely of the centerlines 44. This dual interlocks lends structural strength to the assembly 14, resisting relative movement of the interlocked devices 10 and 12 in a direction (1) transversely of the aligned centerlines 44 (i.e., movement sideways); (2) perpendicularly of the aligned centerlines 44 (i.e., movement up and down); (3) rotationally about the aligned centerlines 44 (i.e., twisting movement); and (4) axially along the aligned centerlines 44 (i.e., movement laterally apart).

However, because the multi-directional fit is frictional, it is releasable. The operator can, with reasonable effort, separate the devices 10 and 12 prior to melting and fusing the regions 40, if desired, without in any way damaging either device 10 and 12.

In the illustrated and preferred embodiment, an annular collar 64 encircles the device 10 and 12. The collar 64 includes a pair of generally planar edges 66 (see, in particular, FIG. 4), which extend perpendicularly relative to the centerline 44 of the planar surface 36, and a pair of generally nonplanar, arcuate surfaces 68, which extend transversely of the centerline 44.

The dissimilar edges 66 and 68 provide a tactile guide for the operator to initially sense, strictly by feel, proper alignment of the devices 10 and 12 in anticipation of forming an assembly 14.

The collar 64 also provides a surface against which an operator can apply pressure to drive the devices 10 and 12 together or to pull the devices 10 and 12 apart prior to melting and fusing the regions 40.

The collar 64 also serves as a means for properly locating the coupled devices 10 and 12 in the energy field intended to melt the regions 40.

More particularly, as shown in FIG. 10, the device 70 used to generate the melting energy includes a base 71 having a pair of spaced apart holders 72. The holders 72 jointly receive the collars 64, but only when the collars 64 are spaced apart the same distance as the holders 72. By purposeful design, when the meltable regions 40 are not in the desired registration, the collars 64 are spaced either farther or closer apart than the holders 72. Thus, when the meltable regions 40 are not in the desired registration, the assembly 14 cannot be physically mounted in the device 70.

The type of energy employed to melt the region 40 of the planar surface 36 can vary.

For example, thermal conduction can be used. In this arrangement (not shown), the energy source constitutes a heat plate or the like in contact with the body 16 of at least one of the devices 10 and 12. The body 16 of the device 10 would, in this embodiment, be made of a thermosetting or high melt point material which would conduct heat energy from the source to the engaged meltable regions 40. The meltable regions 40 would be made of a material having a lower melting temperature than the body 16. The conducted energy would thus melt only the region 40, not the surrounding body 16.

In the illustrated and preferred embodiment, however, thermal radiation is used to heat the meltable region 40. In this arrangement, the body 16 of the device 10 and 12 is made entirely of a thermoplastic material which can be molded by conventional means. The meltable region 40 of at least one of the devices 10 and 12 includes a radiant energy absorbing material which is intermixed with or applied upon the surface of the thermoplastic body material. By applying a sufficient amount of radiant energy, the radiant energy absorbing region 40 is heated until melting occurs. An opening is formed in the region 40. Fluid communication is thereby opened with the associated conduit.

As used herein, the term "radiant energy" broadly refers to energy which is in the form of electromagnetic waves, such as radio waves, infrared waves, visible light, ultraviolet waves, x-rays and the like. Because the transfer of radiant energy requires no intervening medium, the transfer can be faster and more efficient than in conductive or convected heat transfer, both of which require an intervening medium.

Because, in the illustrated and preferred embodiment, thermal radiation is the means employed to heat the overlying regions 40, the body 16 of at least one of the devices 10 or 12 must be capable of transmitting the radiant energy to the meltable regions 40 of the assembly 14.

In the illustrated embodiment, the thermoplastic body 16 of the one device 10 is uniformly absorbant of (i.e., opaque to) the applied radiant energy (see FIGS. 1, 10, and 11). The thermoplastic body 16 of the other device 12 is made of a material which absorbs the applied radiant energy in lesser amounts than the opaque material of the device 10. Preferably, the entire body 16 of this device 12 is relatively nonabsorbant of (i.e., transparent to) the particular type of radiant energy which will be applied.

In this arrangement, as shown in FIG. 10, after the assembly 14 is fitted into the device 70, radiant energy is applied from the source 74 to the assembly 14 through the transparent body 16 of the device 12 and focused upon the meltable regions 40. The source 74 comprises an incandescent quartz lamp which has a tungsten filament operating at about 3150° K. This lamp emits radiant energy which lies in a continuous band encompassing mostly infrared and visible energy, although some ultraviolet radiation is included.

The transparent body 16 is itself not heated to any great extent by the radiant energy. However, in response to the applied thermal radiation, the meltable region 40 of the opaque device 10 is heated to a temperature sufficient to melt the opaque region 40.

Because, in accordance with the invention, the regions 40 are held in intimate contact, the thermoplastic (i.e., meltable) region 40 of the transparent device 12 conducts heat from the opaque region 40 in sufficient quantities to also melt. As a result, the regions 40 jointly melt and fuse together.

In the process of melting, the regions 40 form the opening 42 (see FIG. 11) which establishes through the coupled devices 10 and 12 a fluid path which is hermetically sealed about its periphery.

Because, in accordance with the invention, the coupling means 46 assures the proper alignment between the meltable regions 40, the formed opening is uniform with respect to each region 40, lying along the centerline 44 of each planar surface portion 36.

The particular materials selected for the device 10 and 12 depend largely upon the type of radiant energy which is to be applied.

In the illustrated embodiment, in which infrared and visible light are used, the device 10 and 12 can be made of a material fabricated from poly(4-methyl-1-pentene), which is sold under the trademark TPX by Mitsui Chemical Company. This thermoplastic material has a crystalline melting point of approximately 235° C. and is further discussed in Boggs et al U.S. Pat. No. 4,325,417.

The opaque device 10 includes, intermixed with the TPX material, a charcoal filler. It thus absorbs radiant energy in the infrared and visible light band. The TPX material of the transparent device 12 is free of the filler and is relatively transparent to (i.e., generally nonabsorbant of) this band of radiant energy.

Alternately, as shown in FIG. 12, instead of using the opaque device 10, a device 10a can be used. The device 10a has a body 16 which is uniformly transparent to the passage of the applied radiant energy, like the body of the device 12 as just described. However, in this arrangement, a radiant energy absorbing material 76 is affixed on the external surface of the meltable region 40, for example by hot stamping, printing, gluing, and the like. As before described, thermal radiation will heat the material 76 and cause the region 40 to melt.

Still alternately, two devices 10a can be coupled together to form an assembly 14, with the applied meltable regions 76 position in intimate facing contact.

The size of the mating devices 10 and 12 can vary according to the intended field of use. In a representative embodiment, the overall length of each device 10 and 12 is approximately 1.4 inches, and the maximum outside diameter, exclusive of the collar 64, is about 0.3 inch. In this arrangement, the tab 48 extends about 0.261 inch outwardly from the closed end 24 of the bore 20. Both the tab 48 and the slot 50 have an arcuate surface, respectively 56 and 62, with an approximate slope of 5°. The arcuate surface 56 of the tab 48 has an arc of approximately 0.092 inch radius adjacent to the planar end surface 55. The planar surface 58 of the slot 50 has an arc of approximately 0.112 inch radius at the entrance of the slot 50. The planar surface 54 of the tab 48 is offset from the planar surface portion 36 of the body 18 by about 0.003 inch. In this arrangement, an approximately 0.0012 inch interference fit develops between the tab 48 and slot 50 when the meltable regions are in proper registration.

Various of the features of the invention are set forth in the following claims.

We claim:

1. A fluid transfer device operative by itself to seal the end of a conduit and operative, when two of said devices are connected together and exposed to heat energy, to open a path to conduct fluid between the two devices, said fluid transfer device comprising:

a generally tubular body including a sidewall peripherally enclosing a bore having an open end, which is attachable to the end of the fluid conduit to conduct fluid into said bore, and an oppositely axially spaced closed end, which seals said bore, and, thus, the attached conduit, said sidewall including a generally planar suface portion which has a ceterline extending axially of said bore and which includes a region which is meltable, upon application of the heat energy, to form an opening communicating with said bore, said generally planar surface portion of one of said devices being slidable against said generally planar surface portion of a second one of said devices to bring two of said meltable regions into registration, coupling means comprising a tab portion and a slot portion wherein said tab portion of said one device uniquely mates with a slot portion of said second device, and vice versa, only when said centerlines of said planar surface portions of said two devices align, wherein said tab portion of said coupling means extends axially beyond said closed end of said tubular body and wherein said slot portion of said coupling means spans a section of said planar surface portion, said coupling means being operative, as said tab and slot portions are uniquely mated, for biasing said meltable regions into intimate contact as said registration between said meltable regions occurs and for thereafter releasably interlocking said two devices together to retain said meltable regions in said intimate contact, and wherein said tab portion is resiliently deformable out of a normal portion relative to said tubular body in response to force in a direction transverse of said centerline of said planar surface portion, and wherein said slot portion of said one device deforms said tab portion of the second of said devices out of said normal position, and vice versa, to bias said meltable regions toward said intimate contact, said tab portion being deformed as long as said two devices are releasably interlocked, said meltable regions being operative, when in registration and intimate contact, for jointly melting upon exposure to the heat energy to open a fluid path between said two devices.

2. A fluid transfer device according to claim 1, wherein said tab and said slot portions include mating arcuate surfaces centered with respect to said centerline of said planar surface portion.

3. A fluid transfer device operative by itself to seal the end of a conduit and operative, when two of said devices are connected together and exposed to heat energy, to open a path to conduct fluid between the two devices, said fluid transfer device comprising:

a generally tubular body including a sidewall peripherally enclosing a bore having an open end, which is attachable to the end of the fluid conduit to conduct fluid into said bore, and an oppositely axially spaced closed end, which seals said bore, and, thus, the attached conduit, said sidewall including a generally planar surface portion which has a centerline extending axially of said bore and which includes a region which is meltable, upon application of the heat energy, to form an opening communicating with said bore, said generally planar surface portion of one of said devices being slidable against said generally planar surface portion of a second one of said devices to bring two of said meltable regions in to operative registration, coupling means comprising a tab portion and a slot portion wherein said tab portion of said one device uniquely mates with a slot portion of said second device, and vice versa, only when said centerlines of said planar surface portions of said two devices align, wherein said tab portion of said coupling means extends axially beyond said meltable region of said tubular body and wherein said slot portion of said coupling means spans a section of said planar surface portion, said coupling means being operative, as said tab and slot portions are uniquely mated, for biasing said meltable regions into intimate contact as said registration between said meltable regions occurs and for thereafter releasably interlocking said two devices together to retain said meltable regions in said intimate contact, and wherein said tab portion is resiliently deformable out of a normal position relative to said tubular body in response to force in a direction transverse of said centerline of said planar surface portion, and wherein said slot portion of said one device deforms said tab portion of the second of said devices out of said normal position, and vice versa, to bias said meltable regions toward said intimate contact, said tab portion being deformed as long as said two devices are releasably interlocked, said meltable regions being operative, when in registration and intimate contact, for jointly melting upon exposure to the heat energy to open a fluid path between said two devices.

4. A fluid transfer device operative by itself to seal the end of a conduit and operative, when two of said devices are connected together and exposed to heat energy, to open a path to conduct fluid between the two devices, said fluid transfer device comprising:

a generally tubular body including a sidewall peripherally enclosing a bore having an open end, which is attachable to the end of the fluid conduit to conduct fluid into said bore, and an oppositely axially spaced closed end, which seals said bore, and, thus, the attached conduit, said sidewall including a generally planar surface portion which has a centerline extending axially of said bore and which includes a region which is meltable, upon application of the heat energy, to form an opening communicating with said bore, said generally planar surface portion of one of said devices being slidable against said generally planar surface portion of a second one of said devices to bring two of said meltable regions into operative registration, coupling means comprising a tab portion and a slot portion, wherein said tab portion of said one device uniquely mates with a slot portion of said second device, and vice versa, only when said centerlines of said planar surface portions of said two devices align, said coupling means being operative, as said tab and slot portions are uniquely mated, for biasing said meltable regions into intimate contact as said registration between said meltable regions occurs and for thereafter releasably interlocking said two devices together to retain said meltable regions in said intimate contact, and wherein said tab portion is resiliently deformable out of a normal position relative to said tubular body and wherein said slot portion of said one device deforms said tab portion of the second of said devices out of said normal position, and vice versa, to bias said meltable regions toward said intimate contact, said tab portion being deformed as long as said two devices are releasably interlocked, said meltable regions being operative, when in registration and intimate contact, for jointly melting upon exposure to the heat energy to open a fluid path between said two devices.

5. A fluid transfer device according to claim 4, wherein said tab portion is resiliently deformable in response to a force in a direction transverse of said centerline of said planar surface portion.

* * * * *

UNITED STATES PATENT AND TRADEMARK OFFICE
CERTIFICATE OF CORRECTION

PATENT NO. : 4,611,643

DATED : September 16, 1986

INVENTOR(S) : Susan M. Beebe et al.

It is certified that error appears in the above-identified patent and that said Letters Patent are hereby corrected as shown below:

In Claim 1, at column 9, lines 40-41, change "ceterline" to --centerline--; at column 9, line 66, change "portion" to --position--.

Signed and Sealed this

Twenty-third Day of December, 1986

Attest:

DONALD J. QUIGG

Attesting Officer      Commissioner of Patents and Trademarks